United States Patent
Perrone, Jr. et al.

[19]

[11] Patent Number: 6,074,424
[45] Date of Patent: Jun. 13, 2000

[54] IMPLANTABLE KNEE JOINT PROSTHESIS CONVERTIBLE FROM PRIMARY TO REVISION

[75] Inventors: Charles H. Perrone, Jr., Park City; Aaron Hofmann, Salt Lake City, both of Utah; Charles W. Mumme, Austin, Tex.

[73] Assignee: Sulzer Orthopedics Inc., Austin, Tex.

[21] Appl. No.: 09/012,532

[22] Filed: Jan. 23, 1998

[51] Int. Cl.[7] .................................................. A61F 2/38
[52] U.S. Cl. ................................................. 623/20; 623/18
[58] Field of Search .................................. 623/20, 18, 16

[56] References Cited

U.S. PATENT DOCUMENTS

| | | | |
|---|---|---|---|
| 5,702,460 | 12/1997 | Carls et al. ................................ | 623/20 |
| 5,755,800 | 5/1998 | O'Neil et al. .............................. | 623/20 |
| 5,766,255 | 6/1998 | Slamin et al. ............................. | 623/20 |
| 5,766,257 | 6/1998 | Goodman et al. ......................... | 623/20 |
| 5,782,921 | 7/1998 | Coleran et al. ............................ | 623/20 |
| 5,876,456 | 3/1999 | Sederholm et al. ....................... | 623/16 |

FOREIGN PATENT DOCUMENTS

| | | | |
|---|---|---|---|
| 2 223 174 | 4/1990 | United Kingdom .............. | A61F 2/30 |

Primary Examiner—David H. Willse
Assistant Examiner—Suzette J. Jackson
Attorney, Agent, or Firm—Philip S. Lyren; Kenneth S. Barrow

[57] ABSTRACT

An implantable orthopedic knee joint prosthesis includes a femoral component having an internal box geometry defined by a bone-engaging surface configured as a primary prosthesis. The femoral component has a threaded bore therein communicating with the bone-engaging surface. An adapter has a mating surface complementary to the box geometry of the femoral component and an internal box geometry defined by a bone-engaging surface configured as a revision prosthesis. A hole through the adapter is aligned with the threaded bore of the femoral component and has a recessed shoulder. An adapter screw has a head and a threaded shank, the head sized to be received within the hole of the adapter in engagement with the shoulder, and the shank being sized to be threadedly received within the threaded bore of the femoral component. The adapter screw includes a threaded bore therein. A spacer has a mating surface complementary to the box geometry of the adapter and an internal box geometry defined by a bone-engaging surface configured as a revision prosthesis. The spacer has a hole therethrough aligned with the threaded bore of the adapter screw. A spacer screw has a head and a threaded shank, the shank being sized to be threadedly received within the threaded bore of the adapter screw.

12 Claims, 3 Drawing Sheets

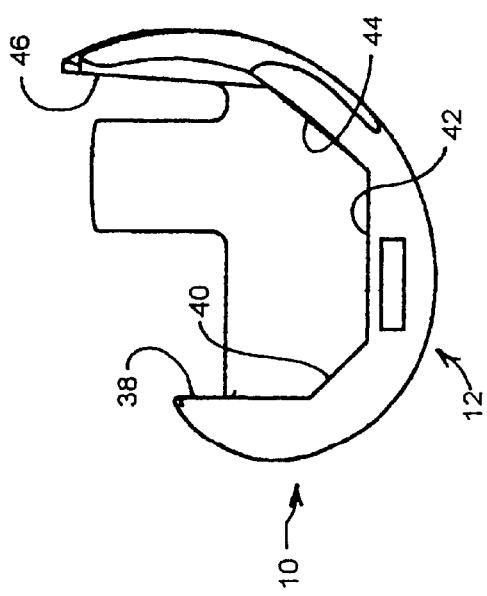
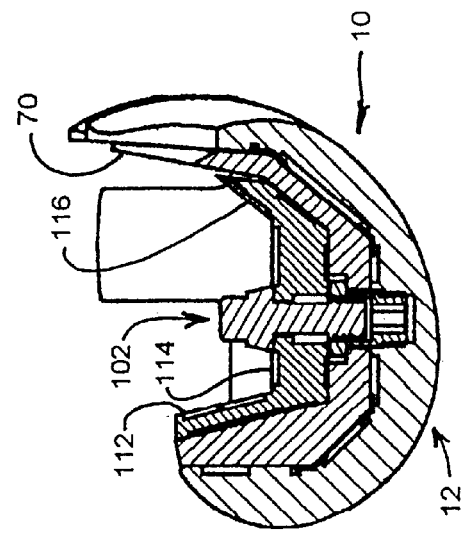
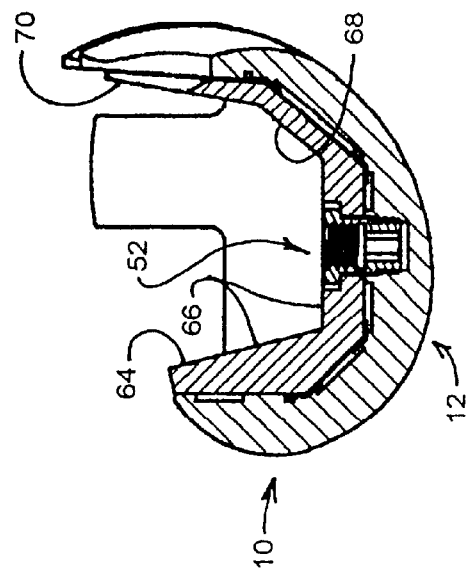

IMPLANTABLE KNEE JOINT PROSTHESIS CONVERTIBLE FROM PRIMARY TO REVISION

BACKGROUND OF THE INVENTION

1. Field of the Invention

The present invention relates generally to implantable prostheses for replacing human skeletal joints, and relates more particularly to a femoral component of an implantable total knee joint prosthesis.

2. Background Art

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma, or congenital defect. Various articulating skeletal joints of the human body are eligible to be fitted with implantable orthopedic prostheses, the knee joint being one of the joints treated most often. The knee joint is a major weight bearing joint and degenerates more quickly than some other joints in case of abnormality. Also, the knee joint plays a critical role in ambulation and quality of life. Consequently, the demand is great for surgical correction of abnormalities of the knee.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction. The condyles join at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

One or more of the articulation surfaces of the knee joint may fail to act normally, requiring the defective natural articulation surface to be replaced with a prosthetic articulation surface provided by an implantable prosthesis. To fit defects of varying scope, while allowing healthy portions of the knee joint to be conserved, a range of types of orthopedic knee implants is available. The range extends from total knee prosthesis systems for replacing the entire articulation surface of each of the femur, tibia and patella, to simpler systems for replacing only the tibiofemoral joint, or only one side (medial or lateral) of the tibiofemoral joint, or only the patellofemoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem received within the medullary canal at the distal end of the femur. The tibial component replaces the proximal end and meniscal articulating surfaces of the tibia and may include a distal stem received within the medullary canal at the proximal end of the tibia. In some designs, the proximal stem of the femoral component or the distal stem of the tibial component is optional and is provided as a modular component. The patellar component replaces the posterior side and natural articulating surface of the patella. Sometimes, the patellar component is not used, and the natural articulating surface of the patella is allowed to articulate against the femoral component. Often, two versions of a particular prosthesis are made available: a "primary" prostheses and a "revision" prostheses. The primary version of the prosthesis is generally more bone conserving than the revision version and is designed with the assumption that it will be the first prosthesis implanted in a patient's knee joint. The revision version is usually used to replace a previously implanted primary prosthesis that has failed. As compared to primary prostheses, revision prostheses replace a greater amount of bone and are usually thicker and have different geometries of the bone-engaging surface.

SUMMARY OF THE INVENTION

In accordance with one aspect of the invention, an implantable orthopedic knee joint prosthesis includes a femoral component having an internal box geometry defined by a bone-engaging surface configured as a primary prosthesis. The femoral component has a threaded bore therein communicating with the bone-engaging surface. An adapter has a mating surface complementary to the box geometry of the femoral component and an internal box geometry defined by a bone-engaging surface configured as a revision prosthesis. A hole through the adapter is aligned with the threaded bore of the femoral component and has a recessed shoulder. An adapter screw has a head and a threaded shank, the head sized to be received within the hole of the adapter in engagement with the shoulder, and the shank being sized to be threadedly received within the threaded bore of the femoral component.

In accordance with another aspect of the invention, the adapter screw includes a threaded bore therein. A spacer has a mating surface complementary to the box geometry of the adapter and an internal box geometry defined by a bone-engaging surface configured as a revision prosthesis. The spacer has a hole therethrough aligned with the threaded bore of the adapter screw. A spacer screw has a head and a threaded shank, the shank being sized to be threadedly received within the threaded bore of the adapter screw.

It is an object of the present invention to provide an implantable orthopedic prosthesis that is convertible from a primary prosthesis to a revision prosthesis.

Other objects and advantages will be apparent from the following descriptions of a preferred embodiment.

BRIEF DESCRIPTION OF THE DRAWINGS

FIG. 2 is a side elevational view of the femoral component of FIG. 1.

FIG. 3 is a side elevational view, partly in section, of the femoral component and the primary-to-revision adapter of FIG. 1.

FIG. 4 is a side elevational view, partly in section, of the femoral component, the primary-to-revision adapter, and the spacer of FIG. 1.

DETAILED DESCRIPTION OF THE PREFERRED EMBODIMENT

Figure 1:
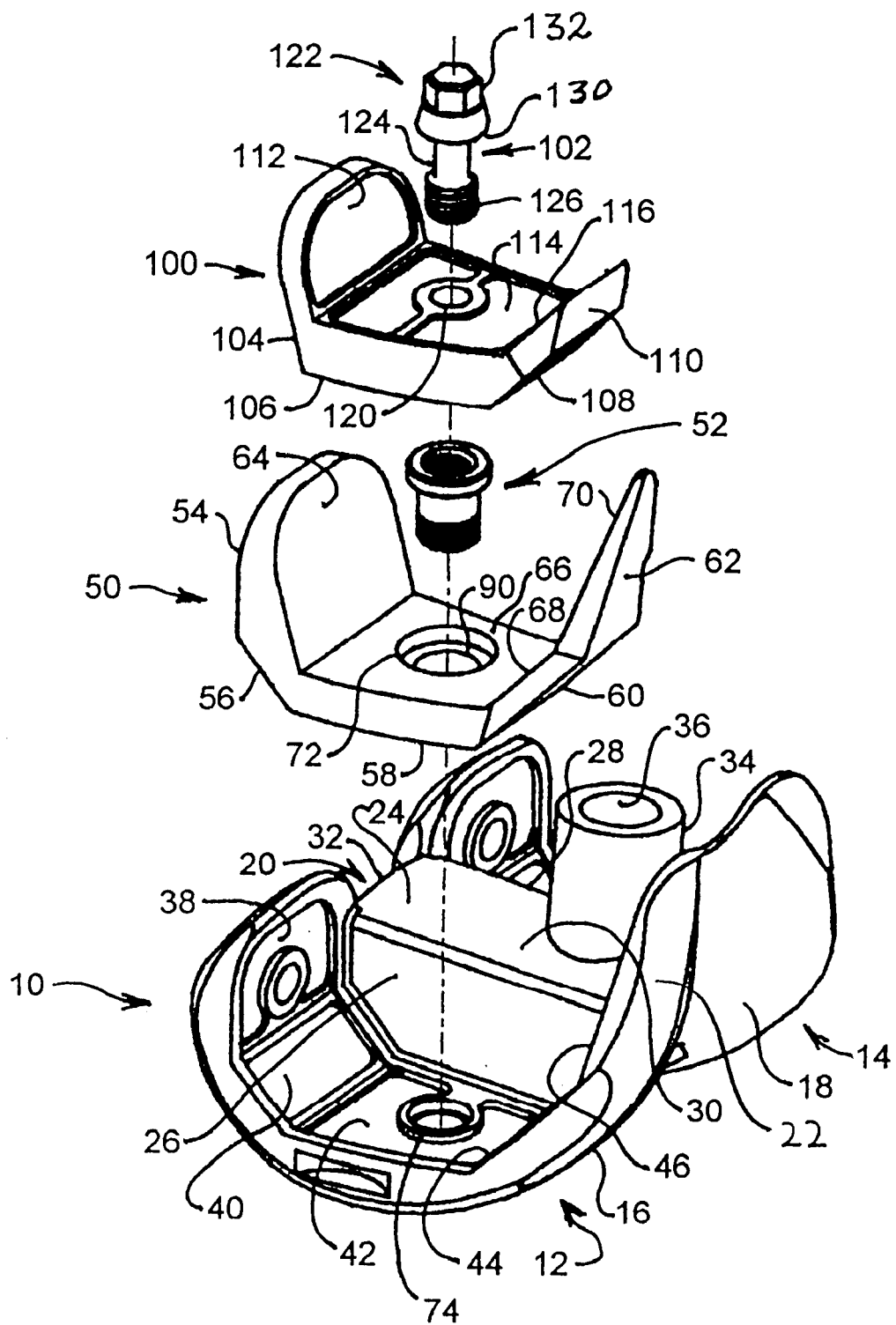
FIG. 1 is an exploded perspective view of a femoral component of an implantable knee joint prosthesis, including a primary-to-revision adapter and a spacer, in accordance with the present invention.
Figure 5:
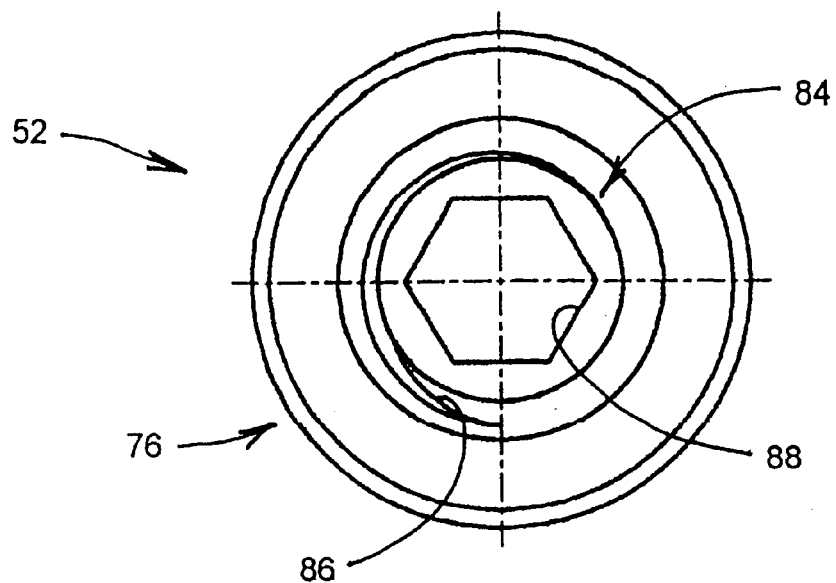
FIG. 5 is an end view of the head of an adapter screw useful with the primary-to-revision adapter and the femoral component of FIG. 1.
Figure 6:
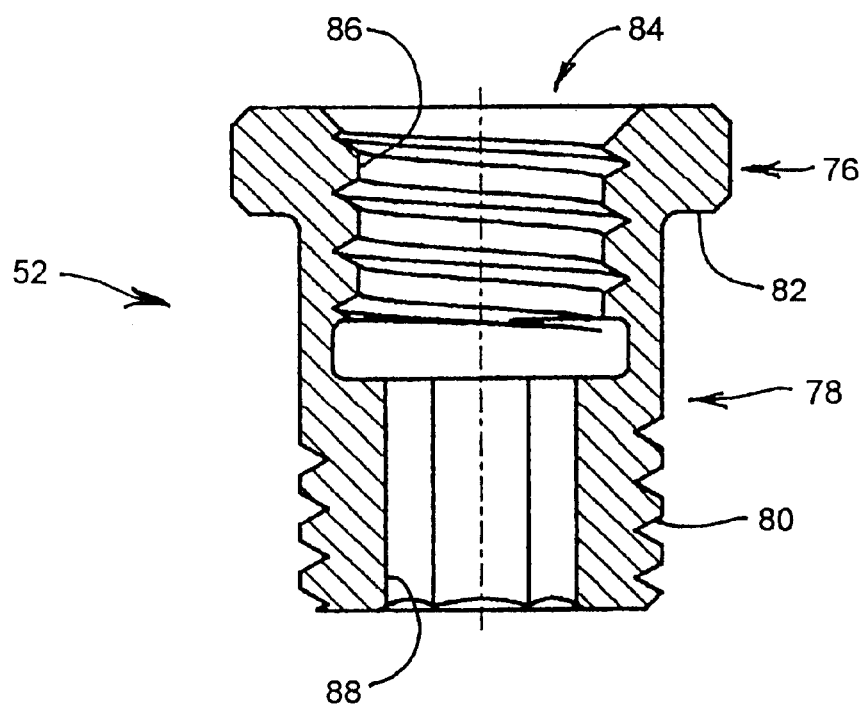
FIG. 6 is a longitudinal sectional view of the adapter screw of FIG. 5.

Referring to FIG. 1, there is illustrated a femoral component 10 of an implantable orthopedic knee joint prosthesis. Femoral component 10 is configured as a posterior stabilized, constrained condylar, primary femoral prosthesis for use with a tibial component having a relatively high central spur that fits closely in the medial-lateral direction between the condyles of the femoral prosthesis. The configuration shown is merely illustrative, and other femoral prosthesis configurations can be employed with the present invention. Femoral component 10 includes condyles 12 and 14, having respective articulating surfaces 16 and 18. Condyles 12 and 14 are separated at the posterior and inferior aspects of femoral component 10 to form an intercondylar groove 20, but are joined at the anterior aspect to form a patellar articulating surface 22. The intercondylar groove 20 between condyles 12 and 14 is covered by a box 24 defined by side walls 26 and 28 rising from the inward edges of condyles 12 and 14, respectively, and a top wall 30. A posterior wall 32 completes box 24 and terminates in a cam follower that engages the eminence of the tibial component (not shown) to provide posterior stabilization. Extending superiorly from top wall 30 of box 24 is a boss 34 having a female conical taper 36 therein for receiving a taper locking male conical taper of a proximal stem (not shown).

Each condyle 12 and 14 has an internal primary box geometry defined by five planar surfaces 38, 40, 42, 44 and 46 that together comprise a primary bone-engaging surface of the prosthesis. The five planar surfaces include posterior surface 38, intermediate posterior surface 40, distal surface 42, intermediate anterior surface 44 and anterior surface 46. During primary implantation surgery, the bone at the distal end of the femur is resected by a plurality of planar saw cuts that intersect to leave a generally convex, polygonal bony surface at the distal end of the femur that is complementary to the internal box geometry of the femoral component 10, and to which the femoral component 10 is mounted directly as a primary prosthesis.

Referring to FIGS. 1–3, femoral component 10 can be converted from a primary prosthesis to a revision prosthesis by thickening the condyles 12 and 14 and modifying the internal box geometry, while leaving the articulating surfaces 16 and 18 unchanged. Conversion from a primary prosthesis to a revision prosthesis is accomplished by securing adapter 50 to femoral component 10 using adapter screw 52. Adapter 50 has an external, generally convex geometry defined by five external planar surfaces 54, 56, 58, 60 and 62 that together comprise an adapter mating surface that is complementary to the internal box geometry of the femoral component 10 defined by surfaces 38, 40, 42, 44 and 46, respectively. Adapter 50 has an internal revision box geometry defined by four planar surfaces 64, 66, 68 and 70 that together comprise a revision bone-engaging surface of the prosthesis. The four planar surfaces include posterior surface 64, distal surface 66, intermediate anterior surface 68 and anterior surface 70. During revision implantation surgery, the bone at the distal end of the femur is resected by a plurality of planar saw cuts that intersect to leave a generally convex, polygonal bony surface at the distal end of the femur that is complementary to the internal box geometry of the adapter 50, and to which the femoral component 10 is mounted via adapter 50 as a revision prosthesis. To secure adapter 50 to femoral component 10 to effect the conversion from a primary to a revision prosthesis, screw 52 is inserted through a hole 72 that passes through the distal wall of adapter 50 defined between surfaces 66 and 58. Screw 52 is received in threaded engagement in internally threaded hole 74 in surface 42 of femoral component 10.

Referring to FIGS. 1, 3, 5 and 6, screw 52 includes a head 76 and a shank 78 having a threaded distal portion 80. The transition between head 76 and shank 78 defines an annular shoulder 82. A bore 84 passes through screw 50 axially, and includes an internally threaded proximal portion 86 and a hexagonally shaped distal portion 88. Threaded proximal portion 86 has an inside diameter larger than the apex-to-apex diameter of the hexagonal portion 88 to permit a hexagonal driving tool to be passed through proximal portion 86 without interference to engage distal hexagonal portion 88. The annular shoulder 82 of screw 50 engages an annular shoulder 90 of adapter 50 to draw adapter 50 into tight engagement with femoral component 10 as screw 52 is threaded into hole 74. Annular shoulder 90 is recessed sufficiently below surface 66 of adapter 50 that head 76 of screw 52 does not protrude above the plane of surface 66 when screw 50 is fully tightened.

Referring to FIGS. 1, 2 and 4, femoral component 10, having been converted from a primary prosthesis to a revision prosthesis by securing adapter 50 to femoral component 10 using adapter screw 52, can be further modified to accommodate cases of exceptional bone loss by securing a spacer 100 to adapter 50 and femoral component 10 using spacer screw 102. Spacer 100 has an external, generally convex geometry defined by four external planar surfaces 104, 106, 108, and 110 that together comprise a spacer mating surface that is complementary to the internal revision box geometry of the adapter 50 defined by surfaces 64, 66, 68 and 70, respectively. Spacer 100 has an internal revision box geometry, substantially the same as that of adapter 50, defined by four planar surfaces 112, 114 and 116 that, together with anterior surface 70 of adapter 50, comprise a revision bone-engaging surface. The four planar surfaces include posterior surface 112, distal surface 114, intermediate anterior surface 116 and anterior surface 70. During revision implantation surgery, the bone at the distal end of the femur is resected by a plurality of planar saw cuts that intersect to leave a generally convex, polygonal bony surface at the distal end of the femur that is complementary to the internal box geometry of the spacer 100, and to which the femoral component 10 is mounted via adapter 50 and spacer 100 as a revision prosthesis. To secure spacer 100 to femoral component 10 and adapter 50, screw 102 is inserted through a hole 120 that passes through the distal wall of spacer 100 defined between surfaces 114 and 106. Screw 102 is received in threaded engagement in internally threaded proximal portion 86 of bore 84 in adapter screw 52.

Again referring to FIG. 1, spacer screw 102 includes a head 122 and a shank 124 having a threaded distal portion 126. The transition between head 122 and shank 124 defines an annular shoulder 130. A proximal portion 132 has an external hexagonal shape for receiving a driving tool having an internal hex. The annular shoulder 130 of screw 102 engages surface 114 surrounding hole 120 to draw spacer 100 into tight engagement with adapter 50 as screw 102 is threaded into threaded portion 86 of adapter screw 52.

The present invention has been illustrated and described with particularity in terms of a preferred embodiment. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

We claim:

1. An implantable orthopedic knee joint prosthesis comprising:
    a femoral component having an internal box geometry defined by a bone-engaging surface configured as a primary prosthesis, said femoral component having a threaded bore therein communicating with said bone-engaging surface;
    an adapter having a mating surface complementary to said box geometry of said femoral component and an internal box geometry defined by a bone-engaging surface configured as a revision prosthesis, said adapter having a hole therethrough aligned with said threaded bore of said femoral component and having a recessed shoulder; and
    a fastener including a head, a shank and a through-bore formed therein, the shank including an external thread for engagement with the threaded bore of the femoral component, the throughbore including an internal thread portion adjacent the head and an internal polygonal surface in the shank adjacent the external thread, the head being sized to be received in the hole of the adapter such that the head engages the shoulder for urging the adapter into engagement with the femoral component.

2. The implantable orthopedic prosthesis of claim 1, in which the head of said screw, when in engagement with said shoulder of said hole of said adapter, does not protrude above the bone-engaging surface of said adapter.

3. The implantable orthopedic prosthesis of claim 1, in which said internal polygonal surface provides a driving surface for receiving a torque imparting tool.

4. The implantable orthopedic prosthesis of claim 2, in which said internal polygonal surface provides a driving surface for receiving a torque imparting tool.

5. The implantable orthopedic prosthesis of claim 1, and further including a spacer having a mating surface complementary to said box geometry of said adapter and an internal box geometry defined by a bone-engaging surface configured as a revision prosthesis, said spacer having a hole therethrough aligned with said internal threaded portion of said fastener; and a screw having a head and a threaded shank, said shank being sized to be threadedly received within said internal threaded portion of said fastener.

6. The implantable orthopedic prosthesis of claim 2, and further including a spacer having a mating surface complementary to said box geometry of said adapter and an internal box geometry defined by a bone-engaging surface configured as a revision prosthesis, said spacer having a hole therethrough aligned with said internal threaded portion of said fastener; and a screw having a head and a threaded shank, said shank being sized to be threadedly received within said internal threaded portion of said fastener.

7. The implantable orthopedic prosthesis of claim 3, and further including a spacer having a mating surface complementary to said box geometry of said adapter and an internal box geometry defined by a bone-engaging surface configured as a revision prosthesis, said spacer having a hole therethrough aligned with said internal threaded portion of said fastener; and a screw having a head and a threaded shank, said shank being sized to be threadedly received within said internal threaded portion of said fastener.

8. The implantable orthopedic prosthesis of claim 4, and further including a spacer having a mating surface complementary to said box geometry of said adapter and an internal box geometry defined by a bone-engaging surface configured as a revision prosthesis, said spacer having a hole therethrough aligned with said internal threaded portion of said fastener; and a screw having a head and a threaded shank, said shank being sized to be threadedly received within said internal threaded portion of said fastener.

9. The implantable orthopedic prosthesis of claim 5 wherein the screw head engages the spacer for urging the spacer into engagement with the adapter.

10. The implantable orthopedic prosthesis of claim 9 wherein the screw head protrudes above the bone-engaging surface of the spacer.

11. An implantable orthopedic knee joint prosthesis convertible from primary to revision comprising:
    a femoral component having an internal box geometry defined by a bone-engaging surface configured as a primary prosthesis, said femoral component having a threaded bore therein communicating with said bone-engaging surface;
    an adapter having a mating surface complementary to said box geometry of said femoral component and an internal box geometry defined by a bone-engaging surface configured as a revision prosthesis, said adapter having a hole therethrough aligned with said threaded bore of said femoral component and having a recessed shoulder; and
    a fastener including a head, a shank and a throughbore formed therein, the shank including an external thread for engagement with the threaded bore of the femoral component, the throughbore including an internal threaded portion and an internal tool gripping surface in the shank adjacent the external thread, the head being sized to be received in the hole of the adapter such that the head engages the shoulder for urging the adapter into engagement with the femoral component, the head also being recessed in the hole of the adapter to permit a revision spacer to be nested in abuttment with the bone-engaging surface of the adapter.

12. An implantable orthopedic knee joint prosthesis convertible from primary to revision comprising:
    a femoral component having an internal box geometry defined by a bone-engaging surface configured as a primary prosthesis, said femoral component having a threaded bore therein communicating with said bone engaging surface;
    an adapter having a mating surface complementary to said box geometry of said femoral component and an internal box geometry defined by a bone-engaging surface configured as a revision prosthesis, said adapter having a hole therethrough aligned with said threaded bore of said femoral component and having a recessed shoulder;

a fastener including a head, a shank and a throughbore formed therein, the shank including an external thread for engagement with the threaded bore of the femoral component, the throughbore including an internal threaded portion and an internal tool gripping surface in the shank adjacent the external thread, the head being sized to be recessed in the hole of the adapter such that the head engages the shoulder for urging the adapter into engagement with the femoral component;

the bone engaging surface of the adapter being configured to receive a revision spacer; and the internal threaded portion of the fastener being provided to receive a threaded member for securing the revision spacer to the bone-engaging surface of the adapter.

* * * * *